US008790931B2

(12) United States Patent
Beebe et al.

(10) Patent No.: US 8,790,931 B2
(45) Date of Patent: Jul. 29, 2014

(54) METHOD OF COLLECTING PARTICLES FROM A SAMPLE FLUID BY ARRANGING THE PARTICLES TO SETTLE AND COLLECT IN A COLLECTING PORTION OF A COLLECTING REGION

(75) Inventors: David J. Beebe, Monona, WI (US); Jay Warrick, Madison, WI (US); Erwin Berthier, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 581 days.

(21) Appl. No.: 12/753,290

(22) Filed: Apr. 2, 2010

(65) Prior Publication Data

US 2011/0244565 A1    Oct. 6, 2011

(51) Int. Cl.
*G01N 1/40*    (2006.01)
*C12Q 1/24*    (2006.01)
*B01L 3/00*    (2006.01)
*G01N 1/38*    (2006.01)

(52) U.S. Cl.
CPC ........... *G01N 1/4077* (2013.01); *B01L 3/50273* (2013.01); *B01L 3/502753* (2013.01); *B01L 3/502761* (2013.01); *C12Q 1/24* (2013.01); *G01N 2001/383* (2013.01); *G01N 2001/4083* (2013.01); *B01L 2300/0803* (2013.01); *B01L 2300/0809* (2013.01)
USPC ........................................ 436/177; 436/174

(58) Field of Classification Search
CPC .......... G01N 1/4077; G01N 2001/383; G01N 2001/4083; B01L 2200/0652; C12Q 1/24
USPC ........... 436/63, 174, 177; 422/502, 503, 527, 422/536, 68.1; 210/767, 787, 788, 800, 210/801, 802, 804, 808
See application file for complete search history.

(56) References Cited

U.S. PATENT DOCUMENTS

2008/0032390 A1 * 2/2008 Meyvantsson et al. .... 435/286.5

OTHER PUBLICATIONS

Pamme, Nicole. "Continuous flow separations in microfluidic devices." Lab on a Chip (2007) 7 1644-1659.*
"Spatiotemporal Micropatterning of Cells on Arbitrary Substrates", Abhyankar et al, Anal. Chem. 2007, 79, 4066-4073.
"Multiphase electropatterning of cells and biomaterils", Albrecht et al, Lab Chip, 2007, 7, 702-709.
"Microfluidic devices for cellomics: a review", Andersson et al, Sensors and Actuators B 92 (2003) 315-325.
"Flow rate analysis of a surface tension driven passive micropump", Berthier et al, Lab Chip, 2007, 7, 1475-1478.
"Computation of transient flow rates in passive pumping microfluidic systems", Chen et al, Lap Chip, 2009, 9, 107-114.

(Continued)

*Primary Examiner* — Christopher A Hixson
(74) *Attorney, Agent, or Firm* — Boyle Fredrickson, S.C.

(57) ABSTRACT

A method is provided for collecting a concentration of particles from a sample fluid containing the particles. The method includes the steps of providing a microfluidic device. The microfluidic device includes an input channel, an output channel and a collection region. The input channel has an input end and an output end. The output channel has an input end and an output end. The collection region interconnects the output end of the input channel and the input end of the output channel. The sample fluid flows through the input channel and the output channel at a first velocity and through the collection region at a second velocity less than the first velocity such that the particles collect in therein.

40 Claims, 3 Drawing Sheets

(56) References Cited

OTHER PUBLICATIONS

"Circulating Tumor Cells, Disease Progression, and Survival in Metastatic Breast Cancer", Cristofanilli et al, New England Journal of Medica 351;8, p. 781, Aug. 19, 2004.

"Cellular observations enabled by microculture: paracrine signaling and population demographics", Domenech et al, Integr. Biol., 2009, 1, 267-274.

"Designing a nano-interface in a microfluidic chip to probe living cells: Challenges and perspectives", Helmke et al, PNAS, vol. 103, No. 17, Apr. 25, 2006, pp. 6419-6424.

"A planar interdigitated ring electrode array via dielectrophoresis for uniform patterning of cells", Hsiung et al, Biosensors and Bioelectronics 24 (2008) 869-875.

"Cells on chips", El-Ali et al, Nature, vol. 442, Jul. 27, 2006, p. 403.

"Manipulation of biological cells using a miroelectromagnet matrix", Lee et al, Applied Physics Letters, vol. 85, No. 6, Aug. 9, 2004, p. 1063.

"Microfluidics meet cell biology: bridging the gap by validation and application of microscale techniques for cell biological assays", Paguirigan et al, BioEssays 30:811-821, 2008.

"Cellular separations: a review of new challenges in analytical chemistry", Pappas et al, Analytica Chimica Acta 601 (2007) 26-35.

"Microfluidic Leukocyte Isolation for Gene Expression Analysis in Critically III Hospitalized Patients", Russon et al, Clinical Chemistry 54:5, 891-900 (2008.

"Analysis of single mammalian cells on-chip", Sims et al, Lap Chip, 2007, 7, 423-440.

"A passive pumping method for microfluidic devices", Walker et al, Lab Chip, 2002, 2, 131-134.

"High-throughput microfluidics: improved sample treatment and washing over standard wells", Warrick et al, Lab Chip, 2007, 7, 316-321.

"A microfluidic processor for gene expression profiling of single human embyonic stem cells", Zhong et al, Lab Chip, 2008, 8, 68-74.

"Laminar Flow Friction and Forced Convection Heat Transfer in Ducts of Arbitrary Geometry", Shah, Int.J.Heat Mass Transfer, vol. 18, pp. 849-862, 1975.

\* cited by examiner

METHOD OF COLLECTING PARTICLES FROM A SAMPLE FLUID BY ARRANGING THE PARTICLES TO SETTLE AND COLLECT IN A COLLECTING PORTION OF A COLLECTING REGION

REFERENCE TO GOVERNMENT GRANT

This invention was made with government support under CA1222672 awarded by the National Institutes of Health. The United States government has certain rights in this invention.

FIELD OF THE INVENTION

This invention relates generally to the concentrating of cell suspensions, and in particular, to a method of a collecting a concentration of particles from a diluted sample fluid and the subsequent gentle treatment of the collected particles.

BACKGROUND AND SUMMARY OF THE INVENTION

Microfluidic devices have shown utility in biochemical analysis by increasing throughput and adding functionality to existing macroscale counterparts. However, "microfluidics" has only recently gained momentum in biological applications, especially in those applications involving cell culture. It is thought that scaling down to the cellular scale (micrometers) will provide more biologically relevant outputs by allowing the cells to communicate and behave more like they would in vivo. Convection can be tightly controlled in microscale devices thereby leaving diffusion as the dominant mode of mass transport. With diffusion as the dominant mode of mass transport, the accumulation of cell secretions is promoted. In addition, the accumulation of soluble factors is further promoted by the increased cell volume ratios of microscale devices (i.e., more cells per microliter (μL) of culture media). As such, microscale culture can offer a more sensitive environment for autocrine and paracrine cell signaling. This increased sensitivity, in turn, allows one to detect biological behavior that is undetectable in macroscale analogs.

One of the main strengths of microscale techniques for biology is the reduced volumes of reagents needed per assay. This benefit is typically discussed as being a source of significant and direct cost savings per endpoint. In the context of cell-based assays, more endpoints can be obtained per cell sample, a fact which is particularly important point in the area of primary cell analysis. Further, by obtaining more endpoints per cell sample, the statistical relevance of results can be directly impacted, specifically in analyses that involve rare cell types or samples with small cell numbers. In the area of clinical diagnostics and monitoring, biopsies and tissue sampling are being pushed to be less invasive. As a result, these procedures typically result in smaller and smaller cell samples. Various types of liquid biopsies often fall into this category such as blood samples from patients with lung, prostate, or breast cancer for analysis of circulating tumor cells (CTCs) or the fluid from bronchoaveolar lavages to diagnose lung cancer. Depending upon the extent of disease and volume of fluid sampled, these types of liquid biopsies may only procure hundreds or thousands of the cell type desired for analysis. With such low numbers of cells, it can be difficult to achieve a robust readout and perform replicates using macroscale techniques. Hence, it can be appreciated that it would be highly desirable to extend the functionality of microfluidic devices to more easily accommodate small numbers of cells and to meet this growing need.

Although it is not often discussed, interfacing limited tissue samples collected using macroscale techniques with microscale devices can pose significant challenges. The first challenge is to seed or place the cells in the device. For many types of microfluidic devices, this often involves the use of tubes and syringe pumps that can act as a barrier for widespread use due to the specialized equipment and expertise required.

A second challenge relates to sample pre-processing. As mentioned previously, microculture devices generally use much higher cell:volume ratios (~5-10 times). For this reason, the densities of cell suspensions are increased accordingly before seeding. However, when the number of cells is extremely small, the corresponding volume of cell suspension for reaching the desired cell density can be too small for typical macroscale prep methods. For this reason, basic centrifugation for pre-concentration has a practical limit in microculture applications using rare cells. For example, if there are less than approximately 50,000 target cells total, centrifugation may be inadequate to supply a high enough cell density for downstream culture or assays of cell function.

Therefore, it is a primary object and feature of the present invention to provide a method of a collecting particles from a sample fluid.

It is a further object and feature of the present invention to provide a method of a collecting particles from a sample fluid that is simpler and less expensive than prior art methods.

It is a further object and feature of the present invention to provide a method of a collecting particles from a sample fluid wherein the density of the particles in the sample fluid is extremely small.

In accordance with the present invention, a method is provided for collecting particles from a sample fluid containing the particles. The method includes the step of providing a microfluidic device having an input channel, an output channel and a collection region. The input channel has an input end and an output end. The output channel has an input end and an output end. The collection region interconnects the output end of the input channel and the input end of the output channel. The sample fluid is flowed through the input channel and the output channel at a first velocity and through the collection region at a second velocity less than the first velocity such that the particles collect in therein.

The method may include the additional steps of filling the input channel, the output channel and the collection region with a fluid. A reservoir drop is deposited on the output end of the output channel and a first pumping drop of the sample fluid is deposited on the input end of the input channel such that the first pumping drop flows through the input channel, the collection region and output channel to the reservoir drop. The reservoir drop is of sufficient dimension to overlap the output end of the output channel and exert an output pressure on the fluid at the output end of the output channel. The first pumping drop exerts an input pressure on the fluid at the input end of the input channel that is greater than the output pressure on the fluid at the output end of the output channel. Thereafter, additional drops of the sample fluid may be sequentially deposited on the input end of the input channel after the first pumping drop flows into the input channel. As a result, a pressure gradient is generated between the fluid at the input end of the input channel and the fluid at the output end of the output channel such that the fluid flows towards the output end of the output channel.

The input channel, the output channel and the collection region have cross-sectional areas. The cross-sectional areas of the input channel and the output channel are less than the cross-sectional area of the collection region. In addition, the input channel, the output channel and the collection region have resistances to flow. The resistances to flow of the input channel and the output channel are greater than the resistance to flow of the collection region.

It is contemplated for the input channel to be a first input channel and the output channel to be a first output channel. The microfluidic device may also include a second input channel and a second output channel. The second input channel has an input end and an output end interconnected to the collection region. The second output channel has an input end connected to the collection region and an output end. The sample fluid also flows through the input channel and the output channel at a first velocity and through the collection region at a second velocity less than the first velocity such that the particles collect in therein.

The output end of the first output channel and the output end of the second output channel may be in fluid communication. The input ends of the first and second input channels may extend radially from a common input port. The collection region may have a generally circular configuration.

In accordance with the present invention, a method is provided for collecting a concentration of particles from a sample fluid containing the particles. The method comprises the steps of: sequentially passing the sample fluid through an input channel having a first cross-sectional area; a collection region having a second cross-sectional area; and an output channel having third cross-sectional area. The cross-sectional area of the collection region is greater than the cross-sectional areas of the input channel and of the output channel. As such, the flow velocities are influenced to allow particles to collect in the collection region.

The input channel has an input end and an output end. The output channel has an input end and an output end. The collection region interconnects the output end of the input channel and the input end of the output channel. The input channel, the output channel and the collection region are filled with a fluid. A reservoir drop is deposited on the output end of the output channel and a first pumping drop of the sample fluid is deposited on the input end of the input channel such that the first pumping drop flows through the input channel, the collection region and output channel to the reservoir drop. The reservoir drop is of sufficient dimension to overlap the output end of the output channel and exert an output pressure on the fluid at the output end of the output channel. The first pumping drop exerts an input pressure on the fluid at the input end of the input channel that is greater than the output pressure on the fluid at the output end of the output channel. Thereafter, a plurality of pumping drops are sequentially deposited at the input end of the input channel after the first pumping drop flows into the first channel. As described, a pressure gradient is created between the fluid at the input end of the input channel and the fluid at the output end of the output channel such that the fluid flows towards the output end of the output channel. The input channel, the output channel and the collection region have resistances to flow. The resistances flow of the input channel and the output channel is greater than the resistance to flow of the collection region.

It is contemplated for the input channel to be a first input channel and the output channel to be a first output channel. As such, the sample fluid is sequentially passed through a second input channel having a cross-sectional area, the collection region, and a second output channel having a cross-sectional area. The first output channel and the second output channel may be in fluid communication. In addition, the first and second input channels may extend radially from a common input port and the collection region may have a generally circular configuration.

In accordance with a further aspect of the present invention, a method is provided for collecting particles from a sample fluid containing the particles. The sample fluid flows through an input channel at a first flow velocity and through a collection region at a second flow velocity less than the first flow velocity such at least a portion of particles in the sample fluid settle in the collection region.

The sample fluid may also be flowed through an output channel downstream of the collection region at a third flow velocity greater than the second flow velocity. The input channel, the collection region and the output channel have resistances to flow. The resistance to flow of the collection region is less than the resistance to flow of the input channel and the output channel. The input channel has an input end and an output end. The output channel has an input end and an output end. The collection region interconnects the output end of the input channel and the input end of the output channel. Thereafter, the input channel, the output channel and the collection region are filled with a fluid. A reservoir drop is deposited on the output end of the output channel and a first pumping drop of the sample fluid is deposited on the input end of the input channel such that the first pumping drop flows through the input channel, the collection region and output channel to the reservoir drop. The reservoir drop is of sufficient dimension to overlap the output end of the output channel and exert an output pressure on the fluid at the output end of the output channel. The first pumping drop exerts an input pressure on the fluid at the input end of the input channel that is greater than the output pressure on the fluid at the output end of the output channel. A plurality of pumping drops may be sequentially deposited at the input end of the input channel after the first pumping drop flows into the first channel. As described, a pressure gradient is generated between the fluid at the input end of the input channel and the fluid at the output end of the output channel such that the fluid flows towards the output end of the output channel.

The input channel, the output channel and the collection region have cross-sectional areas. The cross-sectional areas of the input channel and the output channel are less than the cross-sectional area of the collection region. The input channel may be a first input channel and the output channel may be a first output channel. The sample fluid may be flowed through a second input channel at a fourth flow velocity and through the collection region at the second flow velocity less than the fourth flow velocity such at least a portion of particles in the sample fluid settle in the collection region. In addition, the sample fluid may flow through a second output channel downstream of the collection region at a fifth flow velocity greater than the second flow velocity.

The first output channel and the second output channel may be in fluid communication. The first and second input channels may extend radially from a common input port. The collection region may have a generally circular configuration.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DETAILED DESCRIPTION OF THE DRAWINGS

Figure 1:
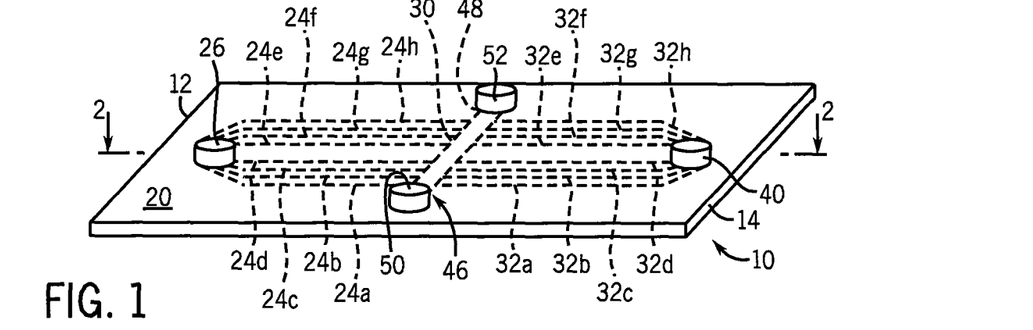
FIG. 1 is an isometric view of a microfluidic device for effectuating the methodology of the present invention.
Figure 2:
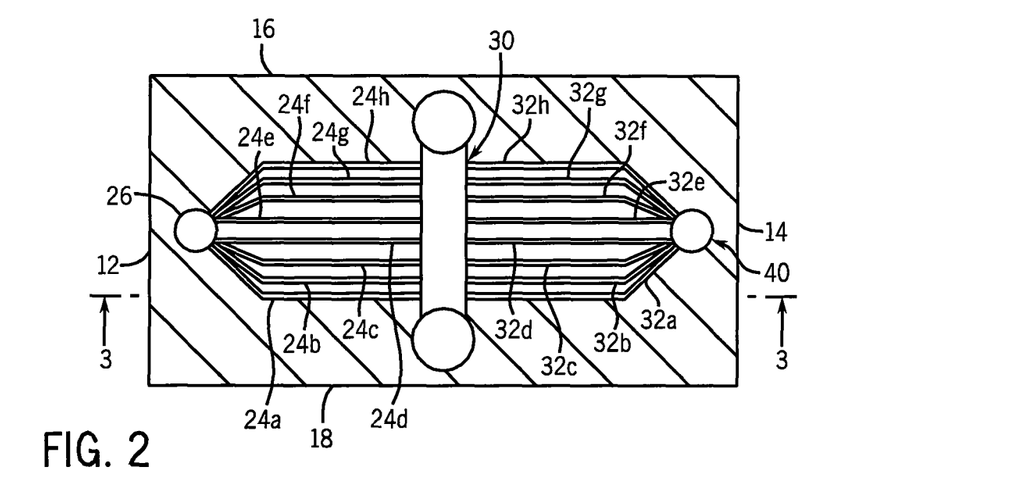
FIG. 2 is a cross sectional view of the microfluidic device taken along line 2-2 of FIG. 1.
Figure 3:
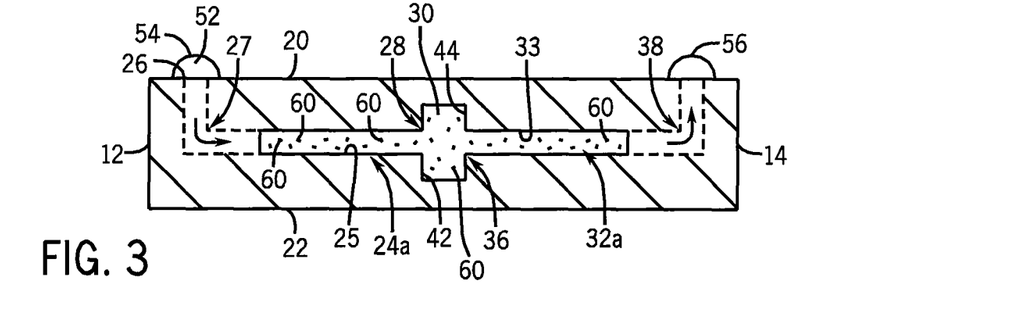
FIG. 3 is a cross sectional view of the microfluidic device taken along line 3-3 of FIG. 2.

Referring to FIGS. 1-3, a microfluidic device for effectuating the methodology of the present invention is generally designated by the reference numeral 10. Microfluidic device 10 may be formed from a variety of material including polydimethylsiloxane (PDMS). Microfluidic device 10 is defined by first and second ends 12 and 14, respectively; first and second sides 16 and 18, respectively; and upper and lower surfaces 20 and 22, respectively. Input port 26 communicates with upper surface 20 of microfluidic device 10 and a plurality of input channels 24a-24h diverge therefrom. The number of input channels 24a-24h can vary. Since each input channel 24a-24h is substantially identical in structure, the following description of input channel 24a is understood to describe input channels 24a-24h as if fully described hereinafter. Input channel 24a is defined by inner surface 25 and includes a first input end 27 communicating with input port 26 and a second opposite output end 28. Output end 28 of input channel 24a communicates with collection chamber 30, for reasons hereinafter described.

Microfluidic device 10 further includes a plurality of output channels 32a-32h extending therethrough that converge at output port 40. Each output channel 32a-32h is substantially identical in structure. As such, the following description of output channel 32a is understood to describe output channels 32b-32h as if fully described hereinafter. Output channel 32a is defined by inner surface 33 and includes first input end 36 communicating with collection chamber 30 and second output end 38. Output end 38 of output channel 32a communicates with output port 40, which in turn, communicates with upper surface 20 of microfluidic device 10. As best seen in FIG. 2, input ends 36 of output channels 32h-32h are axially aligned with corresponding output ends 28 of input channels 24a-24h, for reasons hereinafter described.

Collection chamber 30 is defined by input sidewall 42 that communicates with output ends 28 of input channels 24a-24h and output sidewall 44 that communicates with input ends 36 of output channels 32a-32h. Collection chamber 30 further includes first and second ends 46 and 48, respectively. First and second access ports 50 and 52, respectively, communicate with upper surface 20 of microfluidic device 10 and corresponding ends 46 and 48, respectively, of collection chamber 30 to allow a user access thereto. For reasons hereinafter described, it is intended for the cross-sectional area of collection chamber 30 to be greater than the cross-sectional areas of input channels 24a-24h and output channels 32a-32h.

Modern high-throughput systems are robotic systems designed solely to position a tray (i.e., a multiwell plate or microfluidic device 10) and to dispense or withdraw microliter drops into or out of that tray at user desired locations (i.e., input and output ports 26 and 40, of microfluidic device 10) with a high degree of speed, precision, and repeatability. As is known, the amount of pressure present within a pumping drop 54 of liquid at an air-liquid interface is given by the Young-LaPlace equation:

$$\Delta P = \gamma(1/R1 + 1/R2) \qquad \text{Equation (1)}$$

wherein γ is the surface free energy of the liquid; and R1 and R2 are the radii of curvature for two axes normal to each other that describe the curvature of the surface of pumping drop 54.

For spherical drops, Equation (1) may be rewritten as:

$$\Delta P = 2\gamma/R \qquad \text{Equation (2)}$$

wherein: R is the radius of the spherical pumping drop 54.

From Equation (2), it can be seen that smaller drops have a higher internal pressure than larger drops. Therefore, if two drops of different size are fluidly connected (i.e., via input channels 24a-24h, collection chamber 30 and output channels 32a-32h), the smaller drop will shrink while the larger one grows in size. In view of the foregoing, it can be appreciated that fluid can be pumped through input channels 24a-24h, collection chamber 30 and output channels 32a-32h by using the surface tension in pumping drop 54, as well as, input port 26 and output port 40.

In order to pump fluid through microfluidic device 10, fluid is provided in input channels 24a-24h, collection chamber 30 and output channels 32a-32h of microfluidic device 10. Thereafter, a large reservoir drop 56 is deposited over output port 40. The radius of reservoir drop 56 is greater than the radius of output port 40 and is of sufficient dimension that the pressure at output port 40 is essentially zero. Pumping drop 54, of significantly smaller dimension than reservoir drop 56, is deposited on input port 26 by the robotic micropipetting station. Pumping drop 54 may be hemispherical in shape or may be other shapes. As such, it is contemplated that the shape and the volume of pumping drop 54 be defined by the hydrophobic/hydrophilic patterning of the surface surrounding input port 26 in order to extend the pumping time, if so desired. As heretofore described, microfluidic device 10 is formed from PDMS which has a high hydrophobicity and has a tendency to maintain the hemispherical shapes of pumping drop 54 and reservoir drop 56 on input and output ports 26 and 40, respectively.

Because pumping drop 54 has a smaller radius than reservoir drop 56, a larger pressure exists on input port 26. The resulting pressure gradient causes pumping drop 54 to flow from input port 26 through input channels 24a-24h, collection chamber 30 and output channels 32a-32h towards reservoir drop 56 over output port 40. It can be understood that by sequentially depositing additional pumping drops 54 on input port 26, the resulting pressure gradient will cause the pumping drops 54 deposited on input port 26 to flow through input channels 24a-24h, collection chamber 30 and output channels 32a-32h towards reservoir drop 56 over output port 40. As a result, fluid flows from input port 26 to output port 40.

Alternatively, reservoir drop 56 may be replaced by a "reservoir" at output port 40. More specifically, output port 40 is enlarged to a sufficient radius to accommodate a volume of fluid such that the fluid therein can produce very little pressure due to surface tension. As a result, the resulting pressure gradient will cause pumping drops 54 deposited on input port 26 to flow through input channels 24a-24h, collection chamber 30 and output channels 32a-32h towards enlarged output port 40.

The methodology of the present invention utilizes microfluidic device 10 to "filter" cells 60 out of cell suspension 62 using slow flow to allow them to gently settle into a collection chamber 30, FIG. 3. More specifically, in operation, reservoir drop 56 is deposited on output port 40 and pumping drop 54 of cell suspension 62 is deposited on input port 26 such that the surface tension of the fluid drives cells 60 towards output port 40. Cells 60 are carried from input port 26 via input channels 24a-24h with relatively rapid flow and high resistance as compared to the expansive slow-flow collection chamber 30. The more rapid flow of the fluid through input channels 24a-24h and output channels 32a-32h, as well as, the small dimensions of those channels, keeps cells 60 from adhering to inner surface 25, while the low-velocity flow of the fluid through collection chamber 30 allows cells 30 to settle out of flow and interact with lower surface 64 partially defining collection chamber 30. Non-specific interaction between cells 60 and lower surface 64 is sufficient to keep cells 60 from passing through collection chamber 30 while the fluid, depleted of cells 60, continues to output channels 32a-32h axially aligned with corresponding input channels 24a-24h towards output port 40. Subsequent pumping drops may be deposited at input port 26 of microfluidic device 10 can be used to gently treat or wash collected cells. In this way, cells can be "filtered" or concentrated from dilute cell suspension 62 into collection chamber 30. First and second access ports 50 and 52, respectively, allow a user access to collection chamber 30 to withdraw cells 60 therefrom, apply treatments to cells 60 in a gentle manor or transport cells 60 for processing downstream.

Appropriate cell settling in collection chamber 30 influences the efficiency of microfluidic device 10. For example, if the rate of throughput is too high, cells 60 might pass through collection chamber 30 into output channels 32a-32h to output port 40. If the rate of throughput is too low, processing times become longer and cells 60 might settle out of suspension in input port 26 or input channels 24a-24h before entering collection chamber 30, thereby reducing the efficiency of microfluidic device 10. The main parameters that dictate whether cells 60 settle in collection chamber are flow velocity V; the cell settling rate $V_{set}$; the height h of the collection chamber 30; and the length l of the collection chamber 30. These parameters affect how much time it takes for fluid to pass through collection chamber 30 (hereinafter referred to as the residence time $t_{res}$) and how long it takes a cell to settle (hereinafter referred to as the settling time $t_{set}$) therein.

The fluid velocities through input channels 24a-24h, collection chamber 30 and output channels 32a-32h are different due to difference in the cross-sectional areas of input channels 24a-24h, collection chamber 30 and output channels 32a-32h in a direction perpendicular to flow. More specifically, the velocity of the fluid through a particular region of microfluidic device 10 (namely, input channels 24a-24h, collection chamber 30 and output channels 32a-32h) may be calculated according to the expression:

$$V = Q/A \qquad \text{Equation (3)}$$

wherein: V is the velocity of the fluid through a particular region of microfluidic device 10; Q is the volumetric flow rate of the fluid flowing through a particular region of microfluidic device 10; and A is the cross-sectional area of the particular region of microfluidic device 10 through which the fluid flows. Since the volumetric flow rates Q within input channels 24a-24h and output channels 32a-32h are the same as in collection chamber 30, it can be appreciated that the differences in the cross-sectional area of a region of microfluidic device 10 causes dramatic differences in the velocity of the fluid flowing through each region.

Further, it is noted that the volume of cell suspension 62 that can be processed per unit time in the depicted embodiments is dictated by the number of input channels 24a-24h/output channels 32a-32h and their individual resistances. More specifically, it can be appreciated that the lower total resistance $R_{tot}$ of input channels 24a-24h and of output channels 32a-32h, the increase in the velocity of the fluid flowing therethrough. The resistances $R_{tran}$ of input channels 24a-24h act in parallel with one another. Hence, the total resistance $R_{tot}$ of input channels 24a-24h can be approximated by the expression: $R_{tot}=R_{tran}/n$ wherein n is the number of input channels and assumes the resistance of each transport channel is the same. Likewise, assuming the resistances $R_{tran}$ of the output channels 32a-32h are equal to one another, the total resistance $R_{tot}$ of output channels 32a-32h be approximated by the expression: $R_{tot}=R_{tran}/n$ wherein n is the number of output channels. The number of input channels 24a-24h may differ from the number of output channels 32a-32h without deviating from the scope of the present invention.

Residence time $t_{res}$ can be estimated according to the expression: $t_{res} \approx 1/V$ wherein V is the velocity of the fluid through a particular region of microfluidic device 10. Settling time $t_{set}$ is given by the expression: $t_{set} \approx h/V_{set}$ wherein h is the height of collection chamber 30 and $V_{set}$ is the cell setting rate. Cells 60 that do not have sufficient time to settle to the surface (i.e., $t_{res} < t_{set}$) will pass into output channels 32a-32h to output port 40 and be lost. The actual residence and settling times of a cell depend upon the position of the cell in a flow stream as the cell enters collection chamber 30. Cells 60 entering at a higher point in collection chamber 30 will begin to flow closer to the upper portion of the collection chamber 30 and need a longer distance to settle onto lower surface 64 than those entering on a lower streamline. Worst-case scenarios for residence and settling times may be used to compare the performance of two different collection chamber designs to aid future implementations of the present methodology. In view of the foregoing, it can be appreciated that the dimensions of input channels 24a-24h, collection chamber 30 and output channels 32a-32h must be optimized to insure proper operation of microfluidic device 10.

Figure 4:
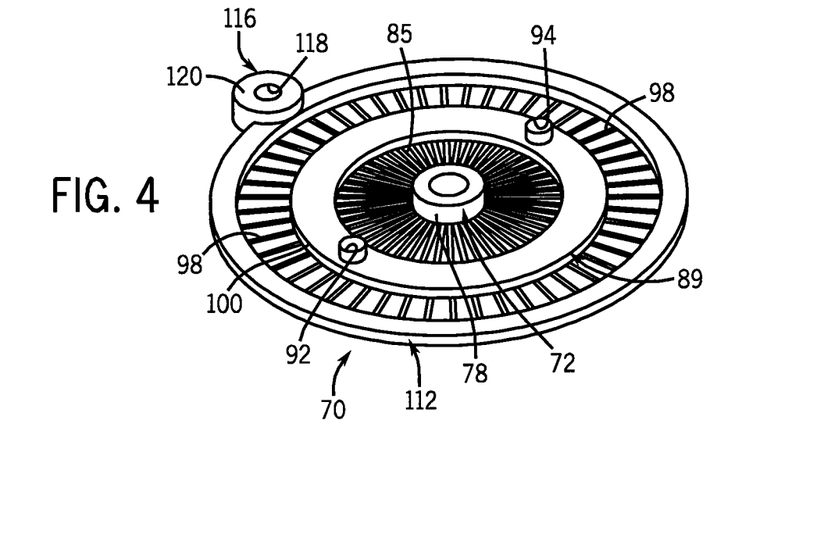
FIG. 4 is an isometric view of an alternate embodiment of a microfluidic device for effectuating the methodology of the present invention.
Figure 5:
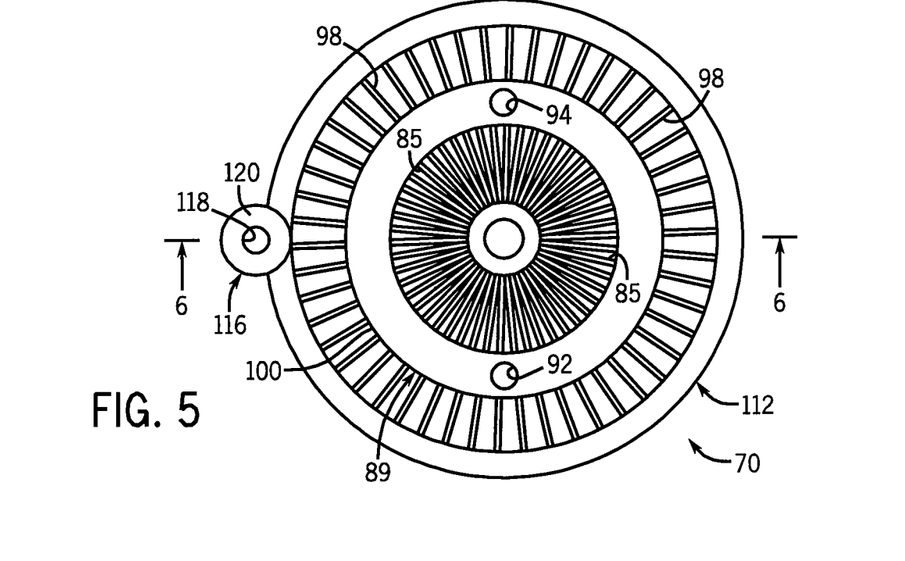
FIG. 5 is a top plan view of the microfluidic device of FIG. 4.
Figure 6:
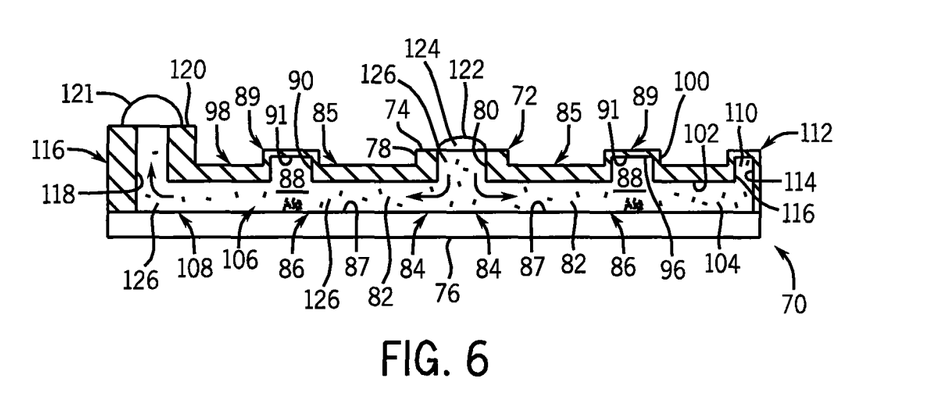
FIG. 6 is a cross sectional view of the microfluidic device taken along line 6-6 of FIG. 5.

Referring to FIGS. 4-6, an alternate embodiment of a microfluidic device for effectuating the methodology of the present invention is generally designated by the reference numeral 70. Microfluidic device 70 may be formed from a variety of materials including polydimethylsiloxane (PDMS). Microfluidic device 70 is by central hub 72 defined by upper surface 74, lower surface 76 and outer periphery 78. A plurality of input spokes 85 extend radially from outer periphery 78 of central hub 72. Input spokes 85 lie in a common plane and include inner surfaces 87 defining input channels 82. Input port 80 communicates with upper surface 74 of microfluidic device 70 and the plurality of input channels 82 extending radially therefrom. The number of input channels 82 can vary and are identical in structure. As such, the following description of a single input channel 82 is understood to describe all of the input channels 82 as if fully described hereinafter. Input channel 82 extends radially from input port 80 along a corresponding axis and includes first input end 84 communicating with input port 80 and a second opposite output end 86. Output end 86 of input channel 82 communicates with collection chamber 88, for reasons hereinafter described.

Microfluidic device 70 further includes inner ring 89 having an inner surface 91 defining a generally ring-shaped collection chamber 88. Inner surface 91 of inner ring 89 is partially defined by inner portion 90 that communicates with output ends 86 of input channels 82. Inner ring 89 further includes circumferentially spaced, first and second access ports 92 and 94, respectively, that communicate with upper surface 96 of inner ring 89 and that allow a user access to collection chamber 88. For reasons hereinafter described, it is intended for the cross-sectional area of collection chamber 88 to be greater than the cross-sectional areas of input channels 82.

Microfluidic device 70 further includes a plurality of output spokes 98 extending radially from outer periphery 100 of inner ring 89. Output spokes 98 are circumferentially spaced about inner ring 89 and lie in a common plane. Output spokes 98 include inner surfaces 102 that define output channels 104. In the depicted embodiment, the number of output spokes 98 is identical to the number of input spokes 85. However, the number of output spokes 98 may differ from the number of input spokes 85 without deviating from the scope of the present invention. It is noted that each of the output channels 104 are identical in structure. As such, the following description of a single output channel 104 is understood to describe all of the output channels 104 as if fully described hereinafter. Output channel 104 extends radially from inner ring 89 along a corresponding axis and includes first input end 106 communicating with collection chamber 88 and a second opposite output end 108. Output end 108 of output channel 104 communicates with output chamber 110, as hereinafter described. For reasons hereinafter described, it is intended for the cross-sectional areas of output channels 104 to be less than the cross-sectional areas of output chamber 110.

Microfluidic device 70 further includes outer ring 112 having inner surface 114 defining generally ring-shaped output chamber 110. Inner surface 114 of outer ring 112 is partially defined by inner portion 116 that communicates with output ends 108 of output channels 104. Outer ring 112 further includes outer hub 116 projecting therefrom. Outer hub 116 defines output port 118 extending therethrough. Output port 118 communicates with upper surface 120 of outer hub 116 and with output chamber 110. For reasons hereinafter described, it is intended for the cross-sectional area of collection chamber 88 to be greater than the cross-sectional areas of input channels 82.

In operation, fluid is provided in input channels 82, collection chamber 88, output channels 104, and output chamber 110 of microfluidic device 70. Reservoir drop 121 is deposited on output port 118 and pumping drop 122 of cell suspension 124 is placed on input port 80 such that the surface tension of the fluid drives cells 126 towards output port 118. Alternatively, instead of reservoir drop 121, output port 118 may be enlarged to a sufficient radius to accommodate a volume of fluid such that the fluid therein has very little surface tension. Cells 126 are carried from input port 80 via input channels 82 with relatively rapid flow and high resistance as compared to the expansive slow-flow collection chamber 88. The more rapid flow of the fluid through input channels 82 keeps cells 126 from adhering to inner surface 87, while the low-velocity flow of the fluid through collection chamber 88 allows cells 126 to settle out of flow and interact with inner surface 91 defining collection chamber 88. Non-specific interaction between cells 126 and inner surface 91 is sufficient to keep cells 126 from passing through collection chamber 88 while the fluid, depleted of cells 126, continues towards output port 118 through output channels 104. While not depicted, it is contemplated for the lower surface portion of inner surface 91 of inner ring 89 to be recessed from inner surfaces 87 and 102 of input and output channels 82 and 104, respectively, to facilitate collection of cells 126 in collection chamber 88.

Subsequent pumping drops may be deposited at input port 80 of microfluidic device 70 can be used to gently treat or wash collected cells. In this way, cells can be "filtered" or concentrated from a dilute suspension into collection chamber 88. First and second access ports 92 and 94, respectively, allow a user access to collection chamber 88 to withdraw cells 126 therefrom, apply treatments to cells 126 in a gentle manor or transport cells 126 for processing downstream. As heretofore described with respect to microfluidic device 10, it can be appreciated that the dimensions of input channels 82, collection chamber 88 and output channels 104 must be optimized to insure proper operation of microfluidic device 70.

Various modes of carrying out the invention are contemplated as being within the scope of the following claims particularly pointing out and distinctly claiming the subject matter, which is regarded as the invention.

We claim:

1. A method for collecting particles from a sample fluid containing the particles, comprising the steps of:
    providing a microfluidic device having:
        an input channel having an input end and an output end;
        an output channel having an input end and an output end; and
        a collection region interconnecting the output end of the input channel and the input end of the output channel, the collection region including a collecting portion in axial alignment with the output end of the input channel and the input end of the output channel; and
    flowing the sample fluid from the input end of the output end of the output channel, the sample fluid simultaneous flowing through the input channel and the output channel at a first velocity and through the collection region at a second velocity less than the first velocity such that the particles settle in and are collected in the collecting portion of the collection region.

2. The method of claim 1 comprising the additional steps of:
    filling the input channel, the output channel and the collection region with a fluid;
    depositing a reservoir drop on the output end of the output channel; and
    depositing a first pumping drop of the sample fluid on the input end of the input channel such that the first pumping drop flows through the input channel, the collection region and output channel to the reservoir drop.

3. The method of claim 2 wherein the reservoir drop is of sufficient dimension to overlap the output end of the output channel and exert an output pressure on the fluid at the output end of the output channel.

4. The method of claim 3 wherein the first pumping drop exerts an input pressure on the fluid at the input end of the input channel that is greater than the output pressure on the fluid at the output end of the output channel.

5. The method of claim 2 comprising the additional step of sequentially depositing a second drop of the sample fluid on the input end of the input channel after the first pumping drop flows into the input channel.

6. The method of claim 2 comprising the additional step of sequentially depositing a plurality of pumping drops at the input end of the input channel after the first pumping drop flows into the first channel.

7. The method of claim 1 comprising the additional steps of:
    filling the input channel, the output channel and the collection region with a fluid; and
    generating a pressure gradient between the fluid at the input end of the input channel and the fluid at the output end of the output channel such that the fluid flows towards the output end of the output channel.

8. The method of claim 1 wherein the input channel, the output channel and the collection region have cross-sectional areas, the cross-sectional areas of the input channel and the output channel being less than the cross-sectional area of the collection region.

9. The method of claim 1 wherein the input channel, the output channel and the collection region have resistances to flow, the resistances to flow of the input channel and the output channel are greater than the resistance to flow of the collection region.

10. The method of claim 1 wherein:
the input channel is a first input channel;
the output channel is a first output channel;
the microfluidic device further includes:
a second input channel having an input end and an output end interconnected to the collection; and
a second output channel having an input end connected to the collection region and an output end;
the sample fluid flows through the second input channel and the second output channel at a first velocity and through the collection region at a second velocity less than the first velocity such that the particles collect in the collection region.

11. The method of claim 10 wherein the output end of the first output channel and the output end of the second output channel are in fluid communication.

12. The method of claim 10 wherein the input ends of the first and second input channels extend radially from a common input port.

13. The method claim 12 wherein the collection region has a generally circular configuration.

14. A method for collecting particles from a sample fluid containing the particles, comprising the steps of:
sequential passing the sample fluid through:
an input channel having a first cross-sectional area;
a collection region having a second cross-sectional area; and
an output channel having third cross-sectional area;
wherein:
the collection region including a collecting portion in axial alignment with the input channel and the output channel;
the cross-sectional area of the collecting portion of the collection region is greater than the cross-sectional areas of the input channel and of the output channel; and
the particles in the sample fluid settle and are collected in the collecting portion of the collection region as fluid flows from the input channel to the collection region and to the output channel.

15. The method of claim 14 wherein:
the input channel has an input end and an output end;
the output channel has an input end and an output end; and
the collection region interconnects the output end of the input channel and the input end of the output channel.

16. The method of claim 15 comprising the additional steps of:
filling the input channel, the output channel and the collection region with a fluid;
depositing a reservoir drop on the output end of the output channel; and
depositing a first pumping drop of the sample fluid on the input end of the input channel such that the first pumping drop flows through the input channel, the collection region and output channel to the reservoir drop.

17. The method of claim 16 wherein the reservoir drop is of sufficient dimension to overlap the output end of the output channel and exert an output pressure on the fluid at the output end of the output channel.

18. The method of claim 17 wherein the first pumping drop exerts an input pressure on the fluid at the input end of the input channel that is greater than the output pressure on the fluid at the output end of the output channel.

19. The method of claim 16 comprising the additional step of sequentially depositing a second drop of the sample fluid on the input end of the input channel after the first pumping drop flows into the input channel.

20. The method of claim 16 comprising the additional step of sequentially depositing a plurality of pumping drops at the input end of the input channel after the first pumping drop flows into the first channel.

21. The method of claim 15 comprising the additional steps of:
filling the input channel, the output channel and the collection region with a fluid; and
generating a pressure gradient between the fluid at the input end of the input channel and the fluid at the output end of the output channel such that the fluid flows towards the output end of the output channel.

22. The method of claim 14 wherein the input channel, the output channel and the collection region have resistances to flow, the resistances flow of the input channel and the output channel is greater than the resistance to flow of the collection region.

23. The method of claim 14 wherein the input channel is a first input channel and the output channel is a first output channel; and wherein the method comprises the additional steps of:
sequentially passing the sample fluid through:
a second input channel having a cross-sectional area; and
the collection region; and
a second output channel having a cross-sectional area.

24. The method of claim 23 wherein the first output channel and the second output channel are in fluid communication.

25. The method of claim 23 wherein the first and second input channels extend radially from a common input port.

26. The method claim 25 wherein the collection region has a generally circular configuration.

27. A method for collecting particles from a sample fluid containing the particles, comprising the steps of:
flowing the sample fluid through an input channel at a first flow velocity;
simultaneous flowing the sample fluid through a collecting portion of a collection region at a second flow velocity less than the first flow velocity such at least a portion of particles in the sample fluid settle and collect in the collection region; and
simultaneous flowing the sample fluid through an output channel downstream of the collection region at a third flow velocity greater than the second flow velocity;
wherein the collecting portion of the collection region is in axial alignment with the input channel and the output channel.

28. The method of claim 27 wherein:
the input channel has a resistance to flow;
the collection region has a resistance to flow;
the output channel has resistance to flow; and
the resistance to flow of the collection region is less than the resistance to flow of the input channel and the output channel.

29. The method of claim 27 wherein:
the input channel has an input end and an output end;
the output channel has an input end and an output end; and
the collection region interconnects the output end of the input channel and the input end of the output channel.

30. The method of claim 29 comprising the additional steps of:
filling the input channel, the output channel and the collection region with a fluid;
depositing a reservoir drop on the output end of the output channel; and
depositing a first pumping drop of the sample fluid on the input end of the input channel such that the first pumping drop flows through the input channel, the collection region and output channel to the reservoir drop.

31. The method of claim 30 wherein the reservoir drop is of sufficient dimension to overlap the output end of the output channel and exert an output pressure on the fluid at the output end of the output channel.

32. The method of claim 31 wherein the first pumping drop exerts an input pressure on the fluid at the input end of the input channel that is greater than the output pressure on the fluid at the output end of the output channel.

33. The method of claim 30 comprising the additional step of sequentially depositing a second drop of the sample fluid on the input end of the input channel after the first pumping drop flows into the input channel.

34. The method of claim 30 comprising the additional step of sequentially depositing a plurality of pumping drops at the input end of the input channel after the first pumping drop flows into the first channel.

35. The method of claim 29 comprising the additional steps of:
filling the input channel, the output channel and the collection region with a fluid; and
generating a pressure gradient between the fluid at the input end of the input channel and the fluid at the output end of the output channel such that the fluid flows towards the output end of the output channel.

36. The method of claim 27 wherein the input channel, the output channel and the collection region have cross-sectional areas, the cross-sectional areas of the input channel and the output channel being less than the cross-sectional area of the collection region.

37. The method of claim 27 wherein the input channel is a first input channel and the output channel is a first output channel; and wherein the method comprises the additional steps of:
flowing the sample fluid through a second input channel at a fourth flow velocity;
flowing the sample fluid through the collection region at the second flow velocity less than the fourth flow velocity such at least a portion of particles in the sample fluid settle in the collection region; and
flowing the sample fluid through a second output channel downstream of the collection region at a fifth flow velocity greater than the second flow velocity.

38. The method of claim 37 wherein the first output channel and the second output channel are in fluid communication.

39. The method of claim 37 wherein the first and second input channels extend radially from a common input port.

40. The method claim 39 wherein the collection region has a generally circular configuration.

* * * * *